(12) United States Patent
Parks

(10) Patent No.: US 7,897,559 B2
(45) Date of Patent: Mar. 1, 2011

(54) DERMATOLOGICAL COMPOSITION AND KIT CONTAINING AVERMECTIN COMPOUND FOR TREATING DERMATOLOGICAL CONDITIONS

(76) Inventor: L. Dean Parks, Ocala, FL (US)

( * ) Notice: Subject to any disclaimer, the term of this patent is extended or adjusted under 35 U.S.C. 154(b) by 528 days.

(21) Appl. No.: 10/730,783

(22) Filed: Dec. 8, 2003

(65) Prior Publication Data

US 2004/0167084 A1 Aug. 26, 2004

Related U.S. Application Data

(63) Continuation-in-part of application No. 10/159,938, filed on Jun. 3, 2002, now abandoned, which is a continuation of application No. 09/976,915, filed on Oct. 12, 2001, now Pat. No. 6,399,651, which is a continuation-in-part of application No. 09/605,747, filed on Jun. 29, 2000, now Pat. No. 6,319,945, application No. 10/730,783, which is a continuation-in-part of application No. 10/161,585, filed on Jun. 3, 2002, now abandoned, which is a continuation of application No. 09/988,914, filed on Nov. 19, 2001, now Pat. No. 6,399,652, which is a continuation-in-part of application No. 09/976,915, filed on Oct. 12, 2001, now Pat. No. 6,399,651, which is a continuation-in-part of application No. 09/605,747, filed on Jun. 29, 2000, now Pat. No. 6,319,945.

(51) Int. Cl.
*A01N 43/42* (2006.01)
*A61K 31/44* (2006.01)
*A01N 61/00* (2006.01)
*A61K 31/00* (2006.01)

(52) U.S. Cl. ............................ 514/1; 514/280
(58) Field of Classification Search .............. 514/453, 514/280; 424/449
See application file for complete search history.

(56) References Cited

U.S. PATENT DOCUMENTS

| 4,310,519 | A | * | 1/1982 | Albers-Schonberg et al. | . 514/30 |
|---|---|---|---|---|---|
| 5,654,312 | A | * | 8/1997 | Andrulis et al. | 514/279 |
| 5,728,719 | A | * | 3/1998 | Miller | 514/360 |
| 5,773,422 | A | * | 6/1998 | Komer | 514/30 |
| 5,786,344 | A | * | 7/1998 | Ratain et al. | 514/100 |
| 5,952,372 | A | * | 9/1999 | McDaniel | 514/453 |
| 6,013,636 | A | * | 1/2000 | Harvey | 514/30 |
| 6,133,310 | A | * | 10/2000 | Parks | 514/453 |
| 6,238,683 | B1 | * | 5/2001 | Burnett et al. | 424/405 |
| 6,262,031 | B1 | * | 7/2001 | Larouche et al. | 514/30 |
| 6,262,117 | B1 | * | 7/2001 | Sefton | 514/558 |
| 6,319,913 | B1 | * | 11/2001 | Mak et al. | 514/179 |
| 6,319,945 | B1 | * | 11/2001 | Parks | 514/453 |
| 6,399,651 | B1 | * | 6/2002 | Parks | 514/453 |
| 6,399,652 | B1 | * | 6/2002 | Parks | 514/453 |
| 6,426,333 | B1 | * | 7/2002 | Huet et al. | 514/30 |
| 6,579,865 | B2 | * | 6/2003 | Mak et al. | 514/179 |
| 2001/0019722 | A1 | * | 9/2001 | Fotinos et al. | 424/448 |
| 2003/0180347 | A1 | * | 9/2003 | Young et al. | 424/449 |

FOREIGN PATENT DOCUMENTS

EP 137627 A2 * 4/1985
WO WO9918800 A1 * 4/1999

OTHER PUBLICATIONS

Youssef et al., Topical application of ivermectin for human ectoparasites, Am. J. Trop. Med. Hyg., 53(6), 1995, pp. 652-653.*
Wilkins et al., Treatment of Psoroptic Mange with Avermectins, Am. J. Vet. Res vol. 41, No1 12, 1980, pp. 2112-2113.*
Giudice, et al, Ivermectin A new therapeutic Weapon in Dermatology?, Arch Dermatology, Jun. 1999, vol. 135, p. 703 & 706.*

* cited by examiner

*Primary Examiner*—Michael G Hartley
*Assistant Examiner*—Melissa Perreira
(74) *Attorney, Agent, or Firm*—Melvin K. Silverman; Yi Li

(57) ABSTRACT

A dermatological composition and a kit containing the composition for treating dermatological conditions including transient acantholytic dermatitis, acne miliaris necrotica, acne varioliformis, perioral dermatitis, acneiform eruptions, acne vulgaris, and seborrheic dermatitis are disclosed. The dermatological composition includes an avermectin compound in an effective amount to treat these dermatological conditions and a pharmaceutically acceptable carrier. The kit includes the dermatological composition integrated in medicated tape, topical dressing, dermal patch, or cleansing tissue.

6 Claims, No Drawings

DERMATOLOGICAL COMPOSITION AND KIT CONTAINING AVERMECTIN COMPOUND FOR TREATING DERMATOLOGICAL CONDITIONS

CROSS REFERENCE TO RELATED APPLICATIONS

This application is a continuation-in-part of co-pending application Ser. No. 10/159,938, filed on Jun. 3, 2002, which is a continuation of application Ser. No. 09/976,915 filed on Oct. 12, 2001, now U.S. Pat. No. 6,399,651, which is a continuation-in-part of application Ser. No. 09/605,747 filed Jun. 29, 2000, now U.S. Pat. No. 6,319,945; and further, this application is a continuation-in-part of co-pending application Ser. No. 10/161,585, filed on Jun. 3, 2002, which is a continuation of application Ser. No. 09/988,914 filed on Nov. 19, 2001, now U.S. Pat. No. 6,399,652, which is a continuation in-part of application Ser. No. 09/976,915 filed on Oct. 12, 2001, now U.S. Pat. No. 6,399,651, which is a continuation-in-part of application Ser. No. 09/605,747 filed Jun. 29, 2000, now U.S. Pat. No. 6,319,945. All prior applications are herein incorporated by reference in their entirety.

FIELD OF THE INVENTION

The present invention relates to a composition and a kit containing the composition for treating dermatological conditions including transient acantholytic dermatitis, acne miliaris necrotica, acne varioliformis, perioral dermatitis, acneiform eruptions, acne vulgaris and seborrheic dermatitis.

BACKGROUND OF THE INVENTION

Transient acantholytic dermatitis, acne miliaris necrotica, acne varioliformis, perioral dermatitis, acneiform eruptions, acne vulgaris, and seborrheic dermatitis are common dermatological diseases. Each has its own etiology and histology.

1. Transient Acantholytic Dermatosis

Transient acantholytic dermatosis, also called syn Grover's disease, is an acquired skin disease which is seen as itchy papules and vesicles resulting in soreness over the area. The lesions appear on the shoulders, neck, thighs, scalp rapidly. Some of the papules can become rough and may have crusting. The disease mostly occurs in meddle to old age, especially in men. Unlike the name of the disease, the condition is not transient, and can last for years.

The cause of the disease is unknown, however, various factors are thought to precipitate the disease, including sun exposure and sun burn, heat exposure, sweating, fever, radiation treatment, and cancers. There is no specific treatment for this disease. Currently, topical steroids, systemic steroids, oral vitamin A, etretinate, PUVA (psoralen and long-wave ultraviolet radiation) and Accutane® (isotretinoin, manufactured by Roche) have been used clinically.

2. Acne Miliaris Necrotica and Acne Varioliformis

Acne miliaris necrotica, also called scalp folliculitis, consists of follicular vesicopustules, frequently solitary, usually very itchy and tender, which appear anywhere in the scalp or adjacent areas. It can range from an occasional nuisance that many people experience to a chronic problem that can be quite troublesome. The severe form of the disease which leaves large scars is called acne varioliformis. The condition is more common in people who are doing activities that make them sweat or who wear occlusive head gear. Stress often seems to trigger outbreaks as well. Existing treatments range from antibiotic shampoos such as Capitrol® (a chloroxine shampoo), astringent compresses, topical antibiotics or steroids to oral antibiotics. In extreme cases, Accutanee has been used, which is well known for the severe adverse side effects that can cause.

3. Perioral Dermatitis

Perioral dermatitis is a chronic papulopustular facial dermatitis. It mostly occurs in younger women. The incidence is estimated as 0.5-1% in industrialized countries, independent of geographical factors. The disease is limited to the skin. Skin lesions occur as grouped follicular reddish papules, papulovesicles and papulopustules on erythematous base with a possible confluent aspect. In an extreme variant of the disease, called lupuslike perioral dermatitis, granulomatous infiltrates occur with a yellowish aspect in diascopy. Although perioral dermatitis is limited to the skin and not life threatening, emotional problems may occur due to the disfiguring character of the facial lesions and a possible prolonged course of the disease.

The etiology of perioral dermatitis is unknown. However, many causative factors have been suggested, including injudicious use of topical steroids, fluorinated toothpaste, skin care ointments and creams, especially with a petrolatum or paraffin base and the vehicle isopropyl myristate, and old or contaminated make-up or applicators. It is known that UV light, heat and wind worsen perioral dermatitis. Further, microbials such as fusiform spirilla bacteria, candida species and other fungi have been found from the lesions. Other microbiological factors, such as candidiasis have been reported to provoke perioral dermatitis. In addition, hormonal factors, and gastrointestinal disturbances have been considered as well.

Known treatments include oral tetracyclines, minocin and doxycycline, with discontinuing topical corticosteroids, and avoiding lauryl sulfate toothpaste. However, it is currently believed there is no medicine that one can apply directly to the skin which will help perioral dermatitis.

4. Acneiform Eruptions

Acneiform eruptions are characterized by papules and pustules resembling acne lesions, not necessarily confined to the usual sites of acne vulgaris. The eruptions are distinguished by their sudden onset, usually in a patient well past adolescence. Most of the acneiform eruptions originate from skin exposure to various industrial chemicals. Some eruptions may come from oral medications. Acneiform eruptions may be induced by exposure of the skin to the fumes generated in the manufacture of chlorine and its by-products. Cutting oils, lubricating oils, crude coal tar applied to the skin for medicinal purposes, have tar distillates, coal tar pitch, and corticosteroids applied to the skin under occlusive dressings, and asbestos are known substances that may produce acneiform eruptions. Some of the acneiform eruptions are induced by medications such as iodides in vitamins with mineral supplement, and bromides in drugs such as propantheline bromide, and corticosteroids.

Although commonly called "trade acne", "bromine acne", and "chloracne", acneiform eruptions are not a true acne, even though they are often ushered in by open comedones. Current treatments of acneiform eruptions include massive keratinization-suppressing doses of vitamin A, 300,000 units daily, topical retinoids, such as Retin-A cream or gel, or even oral Accutane®.

The above-discussed dermatoses are commonly seen clinically. Some patients respond well to the existing treatments. However, many patients suffer from the diseases for many years without significant improvement after being treated with all existing treatments. Furthermore, some patients have adverse reactions to the existing medications, or can not tolerate antibiotics used for treating these dermatoses. Sometimes, it is not appropriate to use existing treatment methods or medications for certain patients. For example, antibiotics and Accutane® are effective for treating acute inflammation caused by these dermatoses, however, they should not be used for pregnant women and nursing mothers. Therefore, there is apparently a need for new and effective topical treatments for the above-mentioned dermatoses.

5. Acne Vulgaris

Acne vulgaris, known as acne by the general public, is a common and multifaceted skin disorder of the hair follicles and sebaceous glands. Although it affects almost 100% of adolescents to varying degrees and generally wanes as adolescence ends, the disease may persist into adulthood. Adult women, in particular, may be affected and may experience premenstrual flares. However, severe acne vulgaris tends to be more common in adolescent males than in people of other age-groups.

At least four factors contribute to the development of acne: follicular plugging, increased sebum production by the sebaceous glands, colonization of the sebaceous follicles with Propionibacterium acnes, and inflammation. Propionibacterium acnes is the most common gram-positive, non-spore forming bacteria, a common resident of the pilosebaceous glands of the human skin. It is the causative agent of acne vulgaris.

Follicular plugging occurs when desquamating cells lining the follicular lumen stick together, rather than flowing to the surface with sebum. This occurs because of abnormal keratinization, components of which are increased cell division and increased cohesiveness of cells lining the follicular lumen. These cells mix with sebum, plug the opening of the hair follicle, and form a closed comedo (commonly called whitehead). If this mixture protrudes from the follicular opening, it turns a dark color (blackheads).

During adolescence, when sebum production increases, the sebaceous follicles become colonized with Propionibacterium acnes. This anaerobic diphtheroid hydrolyzes sebum into free fatty acids, which serve as the primary proinflammatory substances of acne vulgaris. Propionibacterium acnes also secrete chemotactic factors that attract neutrophils. Lysosomal enzyme released from the neutrophils rupture the follicle wall releasing proinflammatory mediators including keratin and lipids into the surrounding dermis. The resulting inflammation forms erythematous papules or pustules, nodules, cysts, or abscesses. If the inflammation is severe, as in cystic acne, the skin may eventually scar.

Therefore, the key features of the pathogenesis of acne vulgaris can be characterized as 1) increased sebum production, 2) hyperkeratinization of the neck of the follicles, 3) bacterial proliferation, and 4) inflammation. Acne vulgaris can be classified into three categories: comedonal, inflammatory, and nodulocystic. Within each category, acne vulgaris can be further divided into mild, moderate, or severe, based on the number of lesions and the amount of skin involved.

Effective management of acne vulgaris can be accomplished by addressing the four key features of the pathogenesis. Topical therapy is usually the first choice for patients with mild-to-moderate inflammatory acne. The use of topical therapy minimizes potential side effects associated with the use of systemic agents. Topical therapies include benzoyl peroxide, which is the most commonly used non-prescription acne medication. It is an important antibacterial oxidizing agent that can decrease the number of Propionibacterium acnes and frequently the amount of free fatty acids. Benzoyl peroxide is the first line monotherapy for mild acne vulgaris and it is available in over-the-counter preparations. Benzoyl peroxide is applied once or twice daily and patients often experience mild redness and scaling of the skin during the first week of usage.

Tretinoin is the most effective topical comedolytic agent currently, decreasing the cohesiveness of follicular epithelial cells, and thereby inhibiting the formation of microcomedones and increasing cell turnover resulting in expulsion of existing comedones. This agent also decreases the thickness of the stratum corneum and potentiates the penetration of topical antibiotic agents. Tretinoin therapy comprises once daily application. Mild redness and peeling are a part of the therapeutic effect of the medication but can result in reduced patient compliance. The improvement may take as long as 6 to 12 weeks, and flare-ups of acne vulgaris can occur during the first few weeks of therapy.

Mild inflammatory acne vulgaris lesions can also be treated with topical antibiotics including erythromycin ointment, clindamycin solution, and meclocylcine cream. The primary action of the antibiotics is to reduce the population of Propionibacterium acnes in the sebaceous follicle and thereby suppress the free fatty acid production. The effectiveness of topical antibiotics in the treatment of acne is limited by their low lipid solubility and subsequent difficulty in penetrating sebum-filled follicles. Topical antibiotics are applied twice daily.

Patients with moderate to severe inflammatory acne often require oral antibiotics in addition to topical therapy. The most commonly prescribed agents include tetracycline, erythromycin, minocycline, and doxycycline. Treatment is usually maintained for several months. Side effects include the overgrowth of nonsusceptible organisms, including Candida, which can produce vaginal and oral yeast infections.

Patients with severe inflammatory acne vulgaris unresponsive to other therapy may require treatment with oral isotretinoin. Isotretinoin is a compound related to vitamin A, and is the only agent that decreases sebum production and reverses the abnormal epithelial formation process. This agent can also decrease number of Propionibacternum acnes in the sebaceous follicle. Duration of therapy is usually 20 weeks, and the satisfactory response rate is quite high. However, treatment is often accompanied by many side effects, including dry skin, pruritus, epistaxis, and photosensitivity, as well as hypertriglyceridemia, abnormal liver function tests, electrolyte imbalances, and elevated platelet counts. Most serious though, is the teratogeric effect of isotretinoin. Use of isotretinoin during pregnancy is absolutely contraindicated. So serious is the potential for death or teratogenic effects to a fetus, isotretinoin is practically contraindicated in women of child-bearing age. Use of isotretinoin must be accompanied by a guarantee by the patient that conception will be avoided at any and all costs.

Because acne vulgaris is a multifactorial disease which is manifest to varying degrees, it is important for the physician to assess the patient to attempt to find therapies which will be helpful to the patient without causing major side effects. All of the current conventional treatments are associated with some degree of adverse side effects that limit their usefulness.

6. Seborrheic Dermatitis

Seborrheic dermatitis, also known as seborrheic eczema and seborrhea, is a chronic superficial inflammatory disease of the skin capable of affecting many parts of the body including the scalp, eyebrows, nasolabial creases, lips, ears, sternal area, axillae, submammary folds, umbilicus, groins, and gluteul crease. The disease is characterized by many shapes, sizes, and surface textures and is often crust-like, yellowish, and accompanied by itching. This is also characterized by remission and exacerbation.

The etiology, pathogenesis and histology of seborrheic dermatitis is unresolved. However, it bears close clinical resemblance to psoriasis and many researchers are of the belief that both conditions share a related etiology, notwithstanding that psoriasis is a broader and less definable condition. Therein, psoriasis typically differentiates over seborrheic dermatitis in its absence of itching and its resistance treatment by compounds, such as, selenium sulfide and zinc pyrithione which have been employed in the treatment of seborrheic conditions.

The preferred compound that is used to illustrate the present invention is ivermectin. Ivermectin is a semi-synthetic derivative of avermectin and is generally produced as a mixture of at least 80% 22,23-dihydroavermectin $B_{1a}$ and less than 20% 22,23-dihydroavermectin $B_{1b}$. The following molecular structure represents the avermectin series of compounds, which can be chemically converted to useful derivatives as discussed below.

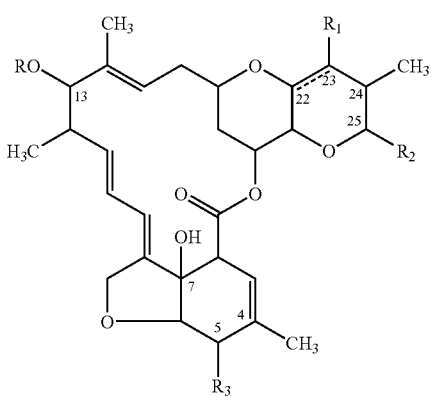

wherein R is the 4'-(alpha-L-oleandrosyl)-alpha-L-oleandrose group of the structure:

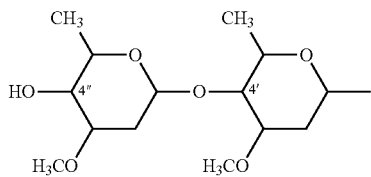

wherein the broken line indicates a single or double bond; $R_1$ is hydroxy and is present only when said broken line indicates a double bond; $R_2$ is isopropyl or sec-butyl; and $R_3$ is methoxy or hydroxy.

The avermectins, of which ivermectin, a chemically produced analog, is a member, are a series of compounds isolated from the fermentation broth of a C-076 producing strain of *Streptomyces avermitillis* and also chemically produced derivatives thereof. There are eight different but closely related compounds are produced by S. avermitillis, designated as $A_{1a}$, $A_{1b}$, $A_{2a}$, $A_{2b}$, $B_{1a}$, $B_{1b}$, $B_{2a}$, and $B_{2b}$. The production of these compounds is described in U.S. Pat. No. 4,310,519. The preparation of ivermectin is disclosed in U.S. Pat. No. 4,199,569. The disclosures of each of the foregoing patents are incorporated herein by reference. The avermectin family of compounds is a series of very potent antiparasitic agents known to be useful against a broad spectrum of endoparasites and ectoparasites in mammals and also to have agricultural uses against various nematode and insect parasites found in and on crops and in soil.

Some of the avermectins contain a 22,23-double bond. This may be selectively reduced to prepare the ivermectin compounds. In addition, the avermectins possess a disaccharide moiety at the 13-position consisting of the alpha-L-oleandrosyl-alpha-L-oleandrosyl group. One or both of these saccharide groups may be removed as described in U.S. Pat. No. 4,206,205, and the produced aglycone derivatives have a hydroxy group at the 13-position. This group may be removed to form the 13-deoxy compound as described in U.S. Pat. Nos. 4,171,314 and 4,173,571; the latter patent also describes the 13-halo derivatives. The avermectin compounds and derivatives have several hydroxy groups which may be acylated as described in U.S. Pat. No. 4,201,861. U.S. Pat. No. 5,055,454 describes invert position 13 of avermectin from a normal alpha stereochemistry to the epimeric 13-beta stereochemistry. U.S. Pat. No. 5,077,308 describes avermectin aglycone derivatives which incorporate a ketal at position 13. U.S. Pat. No. 5,162,363 describes avermectin derivatives where te 23-position ring carbon atom is replaced with by sulfur atom. U.S. Pat. No. 5,229,416 describes avermectin aglycone derivatives which incorporate two fluorine atoms at position 13 and 23. U.S. Pat. No. 5,262,400 describes avermectin compounds that have various substituents at the 4a-position including alkyl, alkoxy alkyl, or polyalkoxy alkyl groups. Other derivatives of avermectin and ivermectin are disclosed in U.S. Pat. Nos. 4,333,925, 4,963,667, 5,114,930, 5,350,742, and 5,830,875. All the aforementioned patents are incorporated herein by reference. The compounds disclosed in the patents mentioned above share the property of antiparasitic activity with ivermectin.

All avermectin compounds mentioned and referred to above share the spectrum of anti-parasitic biological activity of ivermectin, varying only in degree. It is expected that they will share the activity spectrum of ivermectin needed for them being suitable to use for the purpose of the present invention.

Ivermectin has been used as an antiparasitic agent to treat various animal parasites and parasitic diseases since mid-1980's. It is commercially available for animal use as Cardomec (for felines), Eqvalan (for equines) and Ivomec (for bovines) by Merial, a company of Merck Sharp & Dohme and Aventis. The medicine is available in tablets and chewables for heartworm prevention, topical solution for ear mite treatment, or as oral or injectable solution for other parasite problems.

Ivermectin is also commercially available from Merck & Co., Inc for human use as Stromectol® for eradication of threadworm *Strongyloides stercoralis,* and for eradication of *Onchocerca volvulus.* Stromectol® was approved by the U.S. Food and Drug Administration to treat nondisseminated intestinal threadworm (strongyloidiasis) in March 1997. Stromectol® has also been cleared by the U.S. Food and Drug Administration to treat onchocerciasis, or river blindness. The medicine is available in tablets and is orally administered by the patients. The recommended dose of Stromectol® for the treatment of intestinal strongyloidiasis is a single oral dose, two 6 mg tablets for average weight adults (200 micrograms per kilogram of body weight). Stromectol® can also be used in children who weigh 15 kg (33 lb.) or more, at a dose ranging from ½ to 2 tablets.

Magda et al. Amer. J. Trop. Med. Hyg. 53(6) 1995 pp. 652-653 describe a method of topical application of ivermectin to treat head lice. Ivermectin is found to have an absolute curative effect after a single topical application.

U.S. Pat. No. 5,952,372 (to McDaniel) discloses a method of treating a form of rosacea associated with the ectoparasite Demodex by orally administering or topically applying ivermectin to fill and eliminate Demodex Follicuorum mites from hair follicles in affected skin. Such treatment results in cessation of the manifestations of allergic and vasomotor responses to the organism that cause the symptoms and signs of rosacea.

U.S. Pat. No. 6,133,310 (to Parks) discloses a method of treating acne rosacea by topically applying ivermectin to the affected areas. Acne rosacea is a different dermatological disease, in term of etiology, and/or histology, from transient acantholytic dermatitis, acne miliaris necrotica, acne varioliformis, perioral dermatitis, and acneiform eruptions addressed in the present invention. Differential diagnosis is important for the patients to obtain an appropriate treatment and effective prevention of their conditions.

SUMMARY OF THE INVENTION

Accordingly, it is an object of the present invention to provide a dermatological composition and a kit containing the composition for topically treating transient acantholytic dermatitis, acne miliaris necrotica, acne varioliformis, perioral dermatitis, acneiform eruptions, acne vulgaris and seborrheic dermatitis.

In one embodiment, the present invention provides a dermatological composition for topically treating dermatological conditions including transient acantholytic dermatitis, acne miliaris necrotica, acne varioliformis, perioral dermatitis, acneiform eruptions, acne vulgaris and seborrheic dermatitis.

The dermatological conditions comprises an avermectin compound in an amount effective to treat transient acantholytic dermatitis, acne miliaris necrotica, acne varioliformis, perioral dermatitis, acneiform eruptions, acne vulgaris, or seborrheic dermatitis; and a pharmaceutically acceptable carrier. The concentration of the avermectin compound in the dermatological composition can be from about 0.05% to about 8% (w/v). In a preferred embodiment, the concentration of the avermectin compound is in a concentration range from about 0.05% to about 0.5% (w/v).

The avermectin compound includes avermectin, avermectin derivatives, ivermectin, or ivermectin derivatives. In a preferred embodiment, ivermectin is used.

The pharmaceutically acceptable carrier includes water, glycols, alcohols, lotions, creams, gels, emulsions, sprays, shampoos, soaps, body washes, facial cleanser, and facial masks.

In a further embodiment, the present invention provides a kit for topically treating the dermatological conditions. The kit comprises a dermatological composition comprising an avermectin compound in an amount effective to treat transient acantholytic dermatitis, acne miliaris necrotica, acne varioliformis, perioral dermatitis, acneiform eruptions, acne vulgaris, or seborrheic dermatitis, integrated in one form selected from the group consisting of medicated tape, topical dressing, dermal patch, and cleansing tissue.

DETAILED DESCRIPTION OF THE INVENTION

The present invention relates to a dermatological composition for treating transient acantholytic dermatitis, acne miliaris necrotica, acne varioliformis, perioral dermatitis, acneiform eruptions, acne vulgaris, and seborrheic dermatitis.

The avermectin compounds for the purpose of the present invention include avermectin, avermectin derivatives, ivermectin, and ivermectin derivatives. The avermectin compound is preferably mixed with a pharmaceutically acceptable carrier or a base which is suitable for topical application to dermal tissues, to form a dermatological composition. Suitable examples of carrier or base include, but not limited to, water, glycols, alcohols, lotions, creams, gels, emulsions, and sprays. Furthermore, the dermatological composition containing an avermectin compound can be integrated into topic dressing, medicated tape, skin patch, also called dermal patch, and cleansing tissues. Additionally, the avermectin compound can be added into shampoo, soap, body wash, facial cleanser, and facial mask. Examples 1 to 3 provide various topical dermatological compositions containing an avermectin compound for treatment of the above-referenced dermatological conditions.

In a preferred embodiment, ivermectin is used because it is readily available commercially. The concentration of ivermectin in the dermatological composition for the purpose of the present invention can be in a broad range from about 0.05% to 8% weight by volume (w/v). It has been found that a lotion or a cream containing ivermectin at a concentration as low as 0.075% is clinically effective in treating transient acantholytic dermatitis, acne miliaris necrotica, acne varioliformis, perioral dermatitis, acneiform eruptions, acne vulgaris and seborrheic dermatitis.

The treatment method using ivermectin dermatological composition for each of these dermatological conditions is similar. Preferably, in an initial treatment of these dermatological conditions the ivermectin dermatological composition can be applied topically from one to several times daily for a period of from about one week to several weeks, to substantially control the condition and clear the lesions. The initial dosage, including frequency of the topical application, ivermectin concentration of the dermatological composition, and the length of the initial treatment period can be determined depending on a specific disease, severity of the disease, and the response of the patient to the medication. For example, acne miliaris necrotica is more difficult to treat, and it frequently requires an initial treatment of three weeks or longer. While perioral dermatitis patients can respond to ivermectin treatment rapidly, and healing of lesions can occur in less than two weeks. After the initial treatment, a maintenance dosage, that has less frequent application, and/or a dermatological composition with less concentration of ivermectin, can be used for maintaining the condition.

It has been found in an informal clinical trial using the method of the present invention that topical application of ivermectin to skin affected by transient acantholytic dermatitis, acne miliaris necrotica, acne varioliformis, perioral dermatitis, or acneiform eruptions has the following advantageous properties: (1) it removes itching and skin irritation caused by these dermatological conditions; (2) it clears up lesions; (3) it is anti-inflammatory and controls inflammation of the affected area; (4) it has antimicrobial property and controls dermal infection of the affected area; and (5) it is safe and has no side effects observed in any body locations.

The choice of the ivermectin concentration, and the form of the dermatological composition for treatment of a particular condition of the above-referenced dermatological conditions can be made depending on the type and severity of the diseases, location of the affected area, and form of the dermatological composition.

To treat most patients diagnosed with one of the above-mentioned dermatological conditions, a lotion containing about 0.05% to 0.2% of ivermectin can be used. In the case of treating acute conditions, a more potent composition containing higher concentration of ivermectin can be used. On the other hand, for prolonged maintenance of certain conditions, a low concentration such as from about 0.05% to about 0.1% is preferred. Further, a low concentration of ivermectin should be used for pediatric patients.

It is known that some of the diseases, such as perioral dermatitis, the skin on the eyelids can be affected. To treat eyelids, a high concentration of the medicine should be avoided to prevent irritation of the eyes. It is found that a 0.075% ivermectin lotion does not cause eye irritation when it is used on the face, around the eyes, or directly on the eyelids.

In the form of shampoo, soap, facial cleanser, and facial mask the concentration of ivermectin is higher, such as about 2% to about 8%, because the medicine is not retained on the skin after rinsing, and treatment time is short. On the contrary, in the forms of topic dressing, medicated tape, and dermal patch the medicine stays on the treated area longer than other forms, therefore, the concentration of ivermectin can be lower.

The ivermectin shampoo is an appropriate form for treating transient acantholytic dermatitis, acne miliaris necrotica and acne varioliformis, when the affected area is on the scalp. The medicated shampoo can be particularly suitable for maintenance treatment, or prevention of break out for the patients who have chronical history of these diseases.

Optionally, a combination of different forms of topical treatment can also be used. For example, an ivermectin tape can be used in the night, and an ivermectin cream or lotion can be used during the day. The ivermectin shampoo; soap, facial cleanser, and facial mask can be used in combination with any of other topical applications.

The dermatological composition containing ivermectin can be sold as a kit wherein the composition is packaged in a container, such as a plastic container. Instructions on how to use the dermatological composition in accordance with the present invention are included on or associated with the container, which provides detailed instructions for treating transient acantholytic dermatitis, acne miliaris necrotica, acne varioliformis, perioral dermatitis, acneiform eruptions, acne vulgaris, or seborrheic dermatitis.

Although the inventor is not bound by any theoretical explanation as to why the composition and the method of the present invention are effective in treating transient acantholytic dermatitis, acne miliaris necrotica, acne varioliformis, perioral dermatitis, or acneiform eruptions, presentation of certain theoretical understanding may be of value. Based on the clinical observations, it is believed that one reason for the efficacy of the composition and the method of the present invention is due in part to anti-microbial property of ivermectin.

Another possible reason for the efficacy of the composition and the method of the present invention is that the ivermectin dermatological composition has anti-inflammatory effect. It is believed that ivermectin exerts an anti-inflammatory effect on the cells of the sebaceous gland unit, thus decreasing production of neutrophils and lymphocytes which contribute to inflammation.

Ivermectin has been used as an oral medication for treatment of river blindness in human caused by Onchocerca volvulus parasite since late 1980s. With an oral dosage of a moderate ivermectin concentration, this medicine is safe in human, without serious adverse side effects. Therefore, topical treatment of dermatological conditions using ivermectin dermatological composition and the method of the present invention is safe to human patients, which was demonstrated by the clinical examples described hereinafter. Furthermore, as discussed previously that a dermatological composition having ivermectin concentration as low as 0.075% is clinically effective in treating transient acantholytic dermatitis, acne miliaris necrotica, acne varioliformis, perioral dermatitis, acneiform eruptions, acne vulgaris, or seborrheic dermatitis. Such a low concentration is advantageous because it reduces risks of adverse side effects, and reduces the possibility of triggering body's autoimmune responses.

Operating with the informed consent of the patients who had suffered from one of the above-mentioned dermatological conditions, and their conditions had failed to improve by using existing treatment methods or were not appropriate to use existing medications, the patients were treated with the ivermectin dermatological composition and the method of the present invention. Examples 4 to 12 illustrate clinical effectiveness of the method of the present invention.

EXAMPLE 1

A topical dermatological composition containing avermectin compound is obtained as follows.

Mix 0.15 g of ivermectin, manufactured by Merck & Co., Inc., sufficiently with 100 ml of deionized water to make an aqueous suspension, wherein the concentration of ivermectin is 0.15% (w/v). Sodium hydroxide and citric acid can be used to adjusted pH of the suspension to about 7.

Other suitable composition can be made in accordance with Example 1 which include ivermectin in the following concentrations: 0.05%, 0.075%, 0.2%, 0.5%, and 1% (w/v).

EXAMPLE 2

A topical dermatological lotion containing avermectin compound is obtained as follows.

Mix 0.075 g of ivermectin, manufactured by Merck & Co., Inc., sufficiently with 100 ml of Cetaphil® moisturizing lotion, manufactured by Galderma Laboratories, Inc., to make an ivermectin lotion, wherein the concentration of ivermectin is 0.075% (w/v).

Other suitable compositions can be made in accordance with Example 2 which include ivermectin in the following concentrations: 0.05%, 0.1%, 0.2%, 0.5%, 1%, 4%, and 8% (w/v) in the base of Cetaphil® moisturizing lotion. Other compatible commercial available lotions can also be used as a base or carrier.

The Cetaphil® moisturizing lotion is a carrier of the ivermectin, which contains purified water, glycerin, hydrogenated polyisobutene, cetearyl alcohol and ceteareth-20, macadamia nut oil, dimethicone, tocopheryl acetate, stearoxytrimethylsilane and stearyl alcohol, panthenol, farnesol, benzyl alcohol, phenoxyethanol, acrylates/C10-30 alkyl acrylate crosspolymer, sodium hydroxide, citric acid.

EXAMPLE 3

A medicated shampoo containing avermectin compound is obtained as follows.

Mix 3 g of ivermectin, manufactured by Merck & Co., Inc., sufficiently with 100 ml of a shampoo to make an ivermectin shampoo, wherein the concentration of ivermectin is 3% (w/v).

Other suitable compositions can be made in accordance with Example 3 which include ivermectin in the following concentrations of 2%, 5%, and 8% (w/v) in a base of shampoo.

EXAMPLE 4

A 76-year-old male patient presented with several week history of pruritic papules on his chest and back. Topical steroids had no effect. A biopsy showed a papule with mild lymphocytic infiltration and focal areas of epidermal acantholysis. The patient was diagnosed with transient acantholytic dermatosis.

The patient was treated with topical application of the 0.075% ivermectin lotion of Example 2 once to twice daily to wet skin for two weeks, followed with topical application of the lotion once or twice weekly at bed time. The patient was also instructed to stop soap bath, and use weak acetic acids to double rinse clothes to remove all soap. The patient's condition improved significantly in three weeks. The patient was instructed to continue the topical application of the lotion once weekly as needed. In an over two year follow up, the patient had maintained remained symptom free.

EXAMPLE 5

A 63 year old male patient suffered "itchy red bumps" on chest and back persisting for several months. Topical cortisone did not improve the condition. Physical examination found pink to red smooth papules on the chest and back. A biopsy showed only lymphocytic dermal inflammation, no acantholysis was found. The patient was diagnosed with transient acantholytic dermatosis. The patient was treated with topical application of the 0.075% ivermectin lotion of Example 2 twice daily for ten days, followed by twice weekly. The patient had nearly total clearing at his four week follow up visit.

EXAMPLE 6

A 60 year old male had more than fifteen years history of tender "pimples" and sores of the vertex scalp. Many past therapies, including medicated shampoos, oral and topical antibiotics, were of little or no effect. Physical examination found vesico-pustules, crusts and thinning hair on the vertex scalp. The patient was diagnosed with acne miliaris necrotic.

The patient was treated with topically application of the 0.075% ivermectin lotion of Example 2 daily at bed time for three weeks, with a decreased sugar consumption in his diet.

The patient had no new lesions since the first week of treatment. After three weeks treatment, all old lesions were completely healed.

EXAMPLE 7

A 50 year old male patient had a long history of tender sores on the vertex scalp, associated with hair loss. Physical examination found typical vesico pustules of acne miliaris of the vertex scalp, in addition to crusts, excoriations and thinning hair.

The patient was treated topically with the 0.075% ivermectin lotion of Example 2 at bed time for three weeks. The patient's affected skin was totally cleared in three weeks. A maintenance dose of topically applying the ivermectin lotion twice weekly was suggested to the patient for maintenance.

EXAMPLE 8

A 35 year old female patient had five year history of scalp tenderness, associated with tender papules. Many prior therapies failed to treat the condition. The patient was diagnosed with acne miliaris necrotica on the dorsal and vertex scalp.

The patient was treated topically with the 0.075% ivermectin lotion of Example 2 daily at bed time, and washed out in the morning for three weeks. Three weeks later, all lesions were healed.

EXAMPLE 9

A 33-year-old female patient had six-month history of perioral dermatitis, which had its onset during the patient's pregnancy. Previous treatment was withheld because of her pregnancy. At the time of her first visit after the delivery, she was nursing the newborn baby and had transmitted the dermatitis to the baby's lip.

In lieu of using antibiotics because the mother was nursing, a treatment of topical application of the 0.075% ivermectin lotion of Example 2 was given to both mother and the infant daily at bedtime for two weeks. Thereafter, the treatment was reduced to twice weekly. In three weeks, the baby had a total clearing, and discontinued the treatment. The mother had near total clearing, and continued the treatment twice weekly for another three months to insure healing.

EXAMPLE 10

A 68-year-old male patient with persistent perioral scaly papules, was diagnosed with perioral dermatitis. Previously, the patient had adverse reactions to the standard topicals used in this condition, such as benzoyl peroxide, sulfacetamide, Metrogel® from Galderma Laboratories, Inc., and others. In addition, the patient did not tolerate oral antibiotics.

The patient was treated with topical application of the 0.075% ivermectin lotion of Example 2 daily for two weeks. After two weeks, the patient had a total clearing except mild residual erythema, he was ecstatic with the results achieved.

EXAMPLE 11

A 35-year-old female patient had a many year history of firm, tender, or mildly pruritic papulo-nodules on the checks and chin. Past treatments, for acne, were totally ineffective. The patient was diagnosed with acneiform eruptions without specific etiology. The patient had no iodine or bromine exposure.

The patient was treated with topical application of the 0.075% ivermectin lotion of Example 2 daily at bedtime for two weeks, plus elimination of caffeine intake. Thereafter, the dose was reduced to topical application of the lotion twice a week. After four weeks, the patient had near total clearing of the lesions.

EXAMPLE 12

A 36-year-old female patient had a many year history of firm annoying pink nodules of the face. The patient had no history of halogen use. This patient previously used numerous acne lotions and oral tetracycline without effect. The patient was diagnosed with acneiform eruptions.

The patient was treated with topical application of the 0.075% ivermectin lotion of Example 2 daily at bed time for two weeks, followed with topical application of the lotion twice a week. At the four-week return visit, the patient had a total clearing of the lesions.

EXAMPLE 13

A 20 year old pregnant woman developed pustulocystic acne, one type of acne vulgaris, during the latter months of pregnancy. Therapy was limited to topical treatment including benzoyl peroxide, Retin-A (tretinoin), and hydrocortisone lotion. In spite of these treatments, her condition continued to worsen even after delivery. The patient had two large cysts on the right cheek which her physician had scheduled for surgery. Oral antibiotics were not a choice of treatment because she was nursing.

The patient was treated with topical application of the 0.075% ivermectin lotion of Example 2 daily at bed time. In three weeks, her condition improved substantially, and the "cyst surgery" was cancelled because it was no longer needed. A maintenance dosage of topical application of the lotion twice a week was instituted thereafter for four weeks, and the patient had a total clearing.

EXAMPLE 14

A 12 year old girl had extensive comedo-pustular acne (another type of acne vulgaris) on the brow, nose and malar areas. She was treated with Retin-A and benzoyl peroxide. The patient was very distraught because of the redness, inflammation and pustulation. For this reason she was treated with topical application of the 0.075% ivermectin lotion of Example 2 once to twice daily, in addition to her existing conventional treatments. Within two weeks, all of the redness and pustules were gone. Retin-A therapy was continued to the residual comedones.

In the informal trials, no adverse side effects or contraindications were observed among the patients. The patients had no complaints of skin irritation during the initial treatment, or prolonged maintenance treatment. There was no report of increasing skin sensitivity. For the patients who applied the ivermectin lotion topically on the eyelids where the lesions were, there was no eye irritation observed.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

What is claimed is:

1. A dermatological composition for topically treating dermatological conditions comprising transient acantholytic dermatitis, acne miliaris necrotica, acne varioliformis, perioral dermatitis, acneiform eruptions, acne vulgaris, or seborrheic dermatitis, said composition consisting of an avermectin compound in a concentration from 0.05% to 0.1% (w/v) in a lotion consisting of glycerin, hydrogenated polyisobutene, cetearyl alcohol, polyoxyethylene ether of cetyl and stearyl alcohol, macadamia nut oil, dimethicone, tocopheryl acetate, stearoxytrimethylsilane, stearyl alcohol, panthenol, farnesol, benzyl alcohol, phenoxyethanol, acrylates/C10-30 alkyl acrylate crosspolymer, sodium hydroxide, citric acid, and water; said composition not causing skin irritation of patients suffering from said dermatological conditions upon repetitive daily use.

2. The dermatological composition of claim 1, wherein said avermectin compound comprises avermectin, avermectin derivatives, ivermectin, or ivermectin derivatives.

3. The dermatological composition of claim 2, wherein said avermectin compound is ivermectin.

4. The dermatological composition of claim 3, wherein said ivermectin is in a concentration of about 0.075%.

5. The dermatological composition of claim 1, wherein said composition is effective in treating said dermatological conditions.

6. The dermatological composition of claim 1, wherein said composition is integrated in one form selected from the group consisting of medicated tape, topical dressing, dermal patch, and cleansing tissue.

* * * * *